(12) United States Patent
Bergt et al.

(10) Patent No.: US 9,173,559 B2
(45) Date of Patent: Nov. 3, 2015

(54) FIXATION CONTROL DEVICE AND METHOD FOR CONTROLLING THE FIXATION OF AN EYE

(75) Inventors: Michael Bergt, Weimar (DE); Gregor Stobrawa, Jena (DE); Georg Sluyterman Van Langeweyde, Jena (DE); Mark Bischoff, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 900 days.

(21) Appl. No.: 13/379,677

(22) PCT Filed: Jun. 22, 2010

(86) PCT No.: PCT/EP2010/058854
§ 371 (c)(1),
(2), (4) Date: Dec. 21, 2011

(87) PCT Pub. No.: WO2010/149672
PCT Pub. Date: Dec. 29, 2010

(65) Prior Publication Data
US 2012/0133889 A1    May 31, 2012

(30) Foreign Application Priority Data
Jun. 23, 2009 (DE) .......................... 10 2009 030 465

(51) Int. Cl.
*A61B 3/14* (2006.01)
*A61B 3/113* (2006.01)

(52) U.S. Cl.
CPC ..................................... *A61B 3/113* (2013.01)

(58) Field of Classification Search
CPC ......... A61B 3/103; A61B 3/02; A61B 3/1015
USPC .................................. 351/200, 205, 206, 246
See application file for complete search history.

(56) References Cited

U.S. PATENT DOCUMENTS

| 4,836,670 A | 6/1989 | Hutchinson |
| 6,027,216 A | 2/2000 | Guyton et al. |

(Continued)

FOREIGN PATENT DOCUMENTS

| DE | 10001131 | 7/2001 |
| EP | 0990896 | 4/2000 |
| WO | WO 2007/126873 | 11/2007 |

OTHER PUBLICATIONS

Notification of Translation of the International Preliminary Report on Patentability dated Jan. 17, 2012, Internation Bureau of WIPO, Swlitzerland.

(Continued)

*Primary Examiner* — James Greece
(74) *Attorney, Agent, or Firm* — Frommer Lawrence & Haug LLP

(57) ABSTRACT

With some ophthalmological instruments, the patient to be examined or treated needs to gaze in a defined direction. Accordingly, the operator needs the most objective possible information as to whether the patient actually fixates the fixating target or when this may no longer be the case. The invention makes it possible to monitor fixation economically with a short reaction time and with high accuracy. Monitoring of the fixation of an eye is accomplished in an economical manner with a short reaction time and high accuracy through spectroscopic detection of fixation, particularly by identifying a reflection at the fovea or foveola based on different reflectance factors compared to the rest of the retina.

30 Claims, 5 Drawing Sheets

(56) References Cited

U.S. PATENT DOCUMENTS

2004/0252277 A1* 12/2004 Chmielewski et al. ....... 351/209
2006/0142742 A1   6/2006 Donitzky
2006/0200013 A1*  9/2006 Smith et al. .................. 600/319
2007/0236660 A1  10/2007 Fukuma et al.
2008/0084539 A1   4/2008 Daniel

OTHER PUBLICATIONS

International Search Report for Application No. PCT/JP2010/002811 mailed Jul. 13, 2010.

* cited by examiner

FIXATION CONTROL DEVICE AND METHOD FOR CONTROLLING THE FIXATION OF AN EYE

The present application claims priority from PCT Patent Application No. PCT/EP2010/058854 on Jun. 22, 2010, which claims priority from German Patent Application No. DE 10 2009 030 465.7 filed on Jun. 23, 2009, the disclosures of which are incorporated herein by reference in their entirety.

BACKGROUND OF THE INVENTION

1. Field of the Invention

The invention is directed to a fixation monitoring device for an ophthalmological instrument, having a fixating light source for visible light and optics for imaging the fixating light source on a fundus of an eye and to a method for monitoring fixation of the eye.

2. Description of Related Art

With some ophthalmological instruments the patient to be examined or treated needs to gaze in a defined direction. As a rule, this orientation is decisive for the correctness of measurement or therapy and, therefore, for successful treatment. This is particularly true for refractometers, wavefront aberrometers and refractive lasers.

Usually, a visible fixating target which is to be visually fixated by the patient is displayed in the visual field of the patient. Without further action, the operator of the device (i.e., the person performing the examination or treatment) would have to trust the patient to comply with this direction. However, particularly over longer periods of time, there is an increasing likelihood that the patient will fail to maintain the state of fixation. In particular, the human eye can carry out saccadic movements at a speed of up to about 600° per second so that drastic deviations of eye gaze direction can occur within a short time. Lack of certainty with regard to fixation often leads to dispersions in diagnostic or therapeutic findings. It is particularly problematic to maintain and monitor fixation in children, blind persons and persons with other kinds of disabilities. Accordingly, the operator needs the most objective possible information as to whether the patient actually fixates the fixating target or when this may no longer be the case.

To this end, different approaches are known from the prior art. For example, US 2006/0142742 A1 describes a device for ophthalmological treatment having a UV laser in which an additional light beam is provided for visual fixation which generates a light spot on the patient's retina. A camera records an image of a plane of the retina in the region of the fovea centralis (abbreviated as fovea hereinafter). In order to monitor fixation, this image is used for checking whether or not the light spot lies on the fovea. Further, an image of the pupil can be recorded in order to monitor fixation based on the centroid of the pupil or on the relative position of the light spot in relation to the pupil. This type of fixation monitoring has a number of disadvantages. First of all, a two-dimensional image sensor with a high pixel count is obligatory in order to achieve a sufficient accuracy in monitoring. Consequently, the image-taking frequency has an upper limit, for one, because of the lengthy readout of the sensor and, for another, because the subsequent evaluation of at least portions of the image is relatively long owing to the amount of data. The result is a relatively slow reaction to a loss of fixation with the consequent risks during a fast eye movement.

U.S. Pat. No. 6,027,216 describes a method for monitoring fixation in which the fundus is illuminated and radiation that is backscattered from the fundus is picked up by a polarization-sensitive detector. Based on changes in polarization between the illumination light and the backscattered light, it is determined whether the backscattering takes place at the fovea or on the rest of the retina. Backscattering on the fovea is used as an indicator of visual fixation on the part of the patient. It is disadvantageous that polarization-sensitive detection is complicated. In addition, the changes in polarization are minor compared to unwanted influences such as depolarization in the cornea and eye lens so that distinguishing between backscattering on the fovea and on the rest of the retina is fraught with relatively great uncertainty.

SUMMARY OF THE INVENTION

It is the object of the invention to improve an ophthalmological instrument of the type mentioned above and methods for monitoring fixation of the eye so that fixation can be monitored economically with a short reaction time and with high accuracy.

Advantageous embodiments of the invention are indicated in the subclaims.

Monitoring of the fixation of an eye is accomplished in an economical manner with a short reaction time and high accuracy through spectroscopic detection of fixation. Complicated polarization measurements are no longer necessary.

According to the invention, the spectroscopic detection is accomplished in particular by means of at least one measurement light source for emitting at least two wavelengths which have a different ratio of reflectance factors when reflected at a fovea and/or a foveola than when reflected at a retina, optics for imaging the measurement light source on at least a portion of the fundus, and at least one detector for separately acquiring the intensities of the two wavelengths in the form of a respective detector signal after a reflection at the fundus. The measurement light source can be identical to the fixating light source or can be arranged separate therefrom. In this case, the measurement light source itself can in turn comprise two or more individual light sources. The light beams of a plurality of light sources are advisably combined by beam combiners. The two measurement wavelengths can lie in the invisible part of the spectrum, for example, in the infrared region. Only the fixating light source must compulsorily emit light with a visible wavelength (hereinafter referred to also as fixating wavelength). However, when the fixating light source and measurement light source are (at least partially) identical, it is possible to use one or more visible wavelengths of the fixating light source as measurement wavelengths. For example, the fixating light source can emit the first measurement wavelength and the measurement light source can emit the second measurement wavelength, or the measurement light source can also emit the fixating wavelength in addition to the measurement wavelengths, be it one of the measurement wavelengths or an additional wavelength. The fixating light source is preferably at least approximately point-shaped; the measurement light source is also preferably at least approximately point-shaped. The measurement light source is preferably imaged in a point-shaped manner in the fundus and when identical to the fixating light source this condition is necessarily met. The detector then advisably acquires the intensities of the measurement wavelengths which are reflected toward the target location of the point-shaped image on the retina.

The so-called yellow spot (macula lutea) having a diameter of about 3 mm lies in the center of the retina. At its center is located the fovea centralis, a depression having a diameter of approximately 1.5 mm. A fixated object is imaged in the fovea. The spatial resolution of vision is highest at that location. Finally, the foveola having a diameter of about 0.35 mm lies in the center of the fovea. Visual perception takes place in the region of the fovea to a great extent by means of cone cells and in the region of the foveola exclusively by means of cone cells. In the remaining areas of the yellow spot, the density of rods and cones is approximately equal, while the density of cones in the rest of the retina decreases with increasing distance from the yellow spot. The invention is based on the insight that the fovea (and the foveola in particular) has a different spectral reflectivity than the surrounding retina (including the rest of the surface of the macula lutea). Therefore, the location of a reflection can be identified in principle by determining the reflectance factor at a suitable wavelength by comparing the incident intensity with the reflected intensity and comparing this reflectance factor with an expected value. A wavelength is suitable for this purpose when the fovea and/or foveola has a different reflectivity than the rest of the retina at this wavelength. Elaborate polarization measurements are not required.

According to the invention, the at least two measurement wavelengths that are used differ in the ratios of their reflectance factors with respect to the fovea and/or foveola and the rest of the retina. In other words, the condition:

$$R_{\lambda 1, Retina}/R_{\lambda 2, Retina} \neq R_{\lambda 1, Fove(ol)a}/R_{\lambda 2, Fove(ol)a}$$

must be met for the reflectance factor $R_{\lambda 1, Retina}$ of the first wavelength in case of reflection at the retina, for reflectance factor $R_{\lambda 2, Retina}$ of the second wavelength in case of reflection at the retina, for reflectance factor $R_{\lambda 1, Fove(ol)a}$ of the first wavelength in case of reflection at the fovea and/or foveola, and for reflectance factor $R_{\lambda 2, Fove(ol)a}$ of the second wavelength in case of reflection at the fovea and/or foveola.

The specificity of fixation monitoring can be increased through the use of three measurement wavelengths and more. These wavelengths must then satisfy the condition pertaining to the different ratios of their reflectance factors by pairs. According to the invention, it is also possible in principle to use only one individual measurement wavelength which has a different reflectance factor when reflected at the retina than when reflected at the fovea and/or foveola:

$$R_{\lambda, Retina} \neq R_{\lambda, Fove(ol)a}.$$

However, it is then necessary to separate stray light from the detected intensities so that fixation monitoring would be significantly more complicated than if a plurality of wavelengths were used.

Objectively distinguishing between the states of fixation and non-fixation is accomplished in an economical manner, within a short period of time and with high accuracy by identifying the location of reflection (fovea and/or foveola or retina) in that the intensity measurement is carried out, particularly repeatedly, in at least two different measurement wavelengths and a ratio of the two detector signals which correspond to the intensity values is determined and compared with a predetermined value or a predetermined range of values. Depending on the results of the comparison, a result signal is then emitted. The result signal can be an electric, acoustic or electromagnetic, particularly optical, signal. The result signal can assume continuous values or only discrete (e.g., binary) values. The result signal can be scalar or multidimensional. For example, identification of a change from the fixated to the non-fixated state can cause an audible alert to be generated. Alternatively or in addition, the result signal can indicate a distance and particularly a direction between fixating light source and eye gaze direction.

A beam path to the at least one detector and a beam path to the at least one measurement light source are preferably partially identical. The light can be coupled in, for example, by means of a beamsplitter. A fixation monitoring device of this kind can be constructed compactly and also allows a high accuracy in determining the reflectance factors.

In a further development, there is provided a two-dimensional array of detectors with respective detector signals and a correspondingly two-dimensional arrangement of the measurement light source for emitting exclusively invisible measurement wavelengths, wherein the measurement light source at least partially surrounds the fixating light source from the patient's view point. In this way, an indication of direction can be determined for the fovea and/or foveola or the instantaneous gaze direction and in particular can be outputted as a component of the result signal (spatially resolved fixation detection). The detectors are advisably aligned with locations on the retina in a one-to-one correspondence so that the location on the retina where the fovea and/or foveola was imaged can be determined based on the reflectance factors and based on the spatial correlation.

Also advantageous is an alternative embodiment having a plurality of individual measurement light sources which can be imaged in the fundus in a point-shaped manner and which have, respectively, two wavelengths having a different ratio of reflectance factors when reflected at a fovea, particularly a Foveola than when reflected at the rest of the retina, and associated detectors, each of which records the intensities of the measurement wavelengths which are reflected by the respective target location of the point-shaped images on the retina. This embodiment also makes it possible to determine an indication of direction for the fovea and/or foveola or the instantaneous gaze direction and in particular to output it as a component of the result signal. For example, four measurement light sources and associated detectors can be arranged one to each quadrant of the visual field of the patient. In this embodiment, a respective fixating light source is preferably arranged at the location of every measurement light source or the measurement light source serves as fixating light source in that one of the measurement wavelengths or an additional fixating wavelength lies in the visible region of the spectrum.

Embodiment forms which make possible an adjustable projection of the light sources at different visual distances are also advantageous. Vision defects of the patient can be compensated in this way. For example, by imaging the light sources at a suitable distance it is possible for wearers of eyeglasses to use the ophthalmological instrument without eyeglasses.

It is further advantageous to average the detector signals used for the spectroscopic evaluation, or at least a ratio determined therefrom, over a given time period, particularly over a time period that is longer than an average rest period of the eye between saccadic movements of the eye, for example, over a time period of 20 ms to 100 ms. This smoothing serves to improve the signal-to-noise ratio and, therefore, to increase the accuracy of fixation monitoring.

In order to keep the energy of the measuring beam entering the eye low enough to conform to the limiting values of maximum dosage for the eye while still having sufficient intensity available to achieve a good signal-to-noise ratio during detection, the at least one measurement light source can preferably be operated in a pulsed manner at least for the emission of a measurement wavelength. All of the measurement wavelengths can preferably be emitted in a pulsed manner.

The value or value range used for the comparison advisably corresponds to a reflection of the two wavelengths at the fovea, particularly at the foveola. In an economical manner, this yields a binary result signal containing information about whether or not the patient fixates the fixating light source at the moment.

An initial norming of the reflection ratios at the retina and fovea, particularly the foveola, for the individual eye is advantageous in that a first reference value is determined for the ratio of the detector signals during a reflection at the fovea, particularly the foveola, and a second reference value is determined for the ratio of the detector signals during a reflection at the retina. This norming can be made possible, for example, by means of two fixating lights, one on the measurement axis and one off the measurement axis, which are switched on alternately so that the eye can alternately fixate and not fixate. The patient is then initially requested, for example, to look at the one fixating light source on the optical axis of the spectroscopic detection arrangement, whereupon first reference signals are detected and a first reference value for the reflection ratio is determined therefrom. The patient is subsequently asked to look at the other fixating light source located off the optical axis of the spectroscopic detection arrangement, whereupon second reference signals are detected and a second reference value for the reflection ratio is determined therefrom. The first reference value corresponds to the fixated state of the eye to be detected; the second reference value corresponds to the non-fixated state. Based on the two reference values, a criterion for identifying the state of fixation can be determined with high accuracy. For example, the averaged reflection ratio at the fovea and retina determined from the reference values or a given fraction thereof can be specified as a threshold above which a reflection at the fovea (or the foveola) can be deduced.

As an alternative to illumination from different directions with two fixating light sources in which the patient is required to change fixating direction, the reference signals can be acquired from two or more directions simultaneously for norming by using detectors having different orientations. A sequential recording is also possible. Alternatively, the same detector can be used for both reference signals by installing adjustable beam deflecting devices (scanners) and acquiring the reference signals sequentially from different locations of the fundus, for example, from the fovea and/or foveola at one time and from the retina at another time.

Further, it can be decided on the basis of the reference values whether or not the contrast of the reflection ratios between fovea and retina is sufficient for a reliable detection of fixation. For example, the quotient of reference values can be taken and compared with a specified contrast threshold. In case of insufficient contrast (e.g., if it falls below the contrast threshold) due, for example, to a retinal pigment disorder, the operator can be alerted to this and must undertake steps to check fixation manually.

In an advantageous manner, an image recording or a treatment is triggered depending on the result signal, particularly by means of an evaluating unit or a control unit. Added human reaction time is precluded in this way so that the image is recorded or the treatment begun in the fixated state, for example. The advantage of the short delay can generally be achieved, according to the invention, during operation of an ophthalmological instrument by ascertaining that (at least) one eye fixates a fixating target, and an image recording is then made of the eye or treatment of the eye is initiated and/or eye movement tracking is engaged. Correspondingly, the invention also comprises a fixation monitoring device for an ophthalmological instrument, having an evaluating unit which identifies a state in which the eye fixates a fixating target, and an image recording is then made of the eye or treatment of the eye is initiated and/or eye movement tracking is engaged. Movement tracking can be carried out in a known manner, for example, through repeated imaging of the eye pupil. In particular, the image recording or treatment can be interrupted automatically in any case where a loss of fixation is identified. Depending on the type of image recording or treatment, it can be continued if necessary when reestablishment of fixation has been detected.

A valuation and/or weighting of the measurement results and/or of the images of the ophthalmological instrument can be carried out through gradual interpretation of the determined values of the reflection ratios. To this end, the device acquires a series of measurement values and/or images and meanwhile in the manner according to the invention determines for each measurement value and/or for each image the instantaneous reflection ratio as value of the instantaneous degree of fixation and associates the measurement values and/or images with the respective value of the degree of fixation. Based on the respective values of the degree of fixation, a weighted average of the measurement values and/or images recorded by the device can then be determined. For example, this can mean that certain measurement values and/or images of the series are excluded by zero weighting when the degree of fixation is too low. In an extreme case, the individual measurement value or the individual image having the highest degree of fixation is selected from the recorded series and outputted.

In a preferred embodiment form, a modulation of the fixating light source is carried out depending on the result signal. This can also be referred to as feedback of the result signal to the intensity of the fixating light. For example, the fixating light source starts to blink when it is detected that the patient no longer fixates it (i.e., when it is detected that the fixating light is no longer reflected at the fovea). This visual stimulation causes the patient involuntarily to look at the fixating light again.

In an advantageous manner, an intensity modulation of the at least one measurement light source is carried out. In this way, only one detector is needed to measure the intensities of the two (or more) measurement wavelengths. This is accomplished either by modulation with different frequencies for the wavelengths and detection of the reflected measurement wavelengths in a common detector, wherein the respective detector signals are subsequently separated electronically through lock-in technique, for example, or by modulation with an identical frequency for the wavelengths with offset phases and phase-sensitive detection of the wavelengths in a common detector.

An embodiment having confocal detection in the at least one detector is particularly preferred. Confocal detection at a point conjugate to the relevant reflection location makes it possible to measure the reflectance factors with high spatial resolution.

In a further development of the invention, the recording of an image of an iris is carried out by means of a camera to determine a relative position of a pupil, particularly a pupil center, in relation to a vertex of a cornea with respect to an optical reference axis. The instantaneous vertex V is that point on the cornea which lies closest to the camera along the optical reference axis. In other words, the vertex with respect to the optical axis is that point on the surface whose orthogonal projection on the optical axis is at the shortest distance from the entrance optics of the camera. Alternatively, it may be defined as a ceiling (highest point) in the viewing direction of the optical axis of the camera or as a local maximum or extremum with respect to the optical axis of the camera. The location of the vertex is advisably determined based on a Purkinje reflex at the cornea. This is carried out when the fixating of the fixating light source has been identified by the fixation monitoring device according to the invention either by means of the fixation monitoring device itself or by means of the parent ophthalmological instrument. In this way, the determined pupil-vertex relationship can be correlated to the gaze direction associated with the identified fixation. Since the positional relationship of the pupil and vertex changes as the gaze direction changes, the image recorded in the state identified as the fixation state or the pupil-vertex relationship determined therefrom can be used as reference for a corrected fixation. In some diagnostic and therapeutic methods, the instantaneous pupil-vertex relationship is determined for other purposes and accordingly can also be used for fixation monitoring. Particularly in embodiments with spatially resolved fixation detection, a plurality of pupil-vertex relationships (particularly in the form of iris images) can be determined for different fixation directions and stored. When there is a sufficient number and density of control points of this kind, a detection of eye movements can be carried out, for example, by interpolation. In an advantageous manner, one or more pupil-vertex relationships can be determined regardless of subsequent use, particularly preoperatively.

The fixation monitoring device can advantageously be constructed in a binocular manner so that the fixation of two eyes can be monitored simultaneously. This can be used in equipment performing binocular eye measurements. For example, fixation detection on two sides can be used for analyzing stereoscopic vision or a defective position of the eyes (strabismus). To this end, the spatially resolved fixation monitoring in particular can be used to determine the gaze direction.

In an advantageous feature, the fixation monitoring device according to the invention is constructed as a module so that conventional fixating light sources can be replaced with little effort.

The invention also includes an ophthalmological instrument having a fixation monitoring device according to the invention and computer programs or evaluating units which are designed to carry out a method according to the invention. To this end, a computer program can comprise, for example, a software module for illumination by means of at least one measurement light source of at least a portion of a fundus with light of two wavelengths which have a different ratio of reflectance factors when reflected at a fovea, particular a foveola, than when reflected at a retina, a software module for separate detection of the intensities of two wavelengths by means of at least one detector as respective detector signal after reflection at a fundus, a software module for determining a ratio of the two detector signals, a software module for comparing the ratio with a given value or a given value range, and a software module for outputting a result signal depending on the comparison results. In this regard, an individual software module can carry out all of the tasks mentioned above. Alternatively, at least one individual software module can carry out some of the above tasks. But there can also be five or more different software modules.

BRIEF DESCRIPTION OF THE DRAWINGS

Identical parts have the same reference numbers in all of the drawings.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
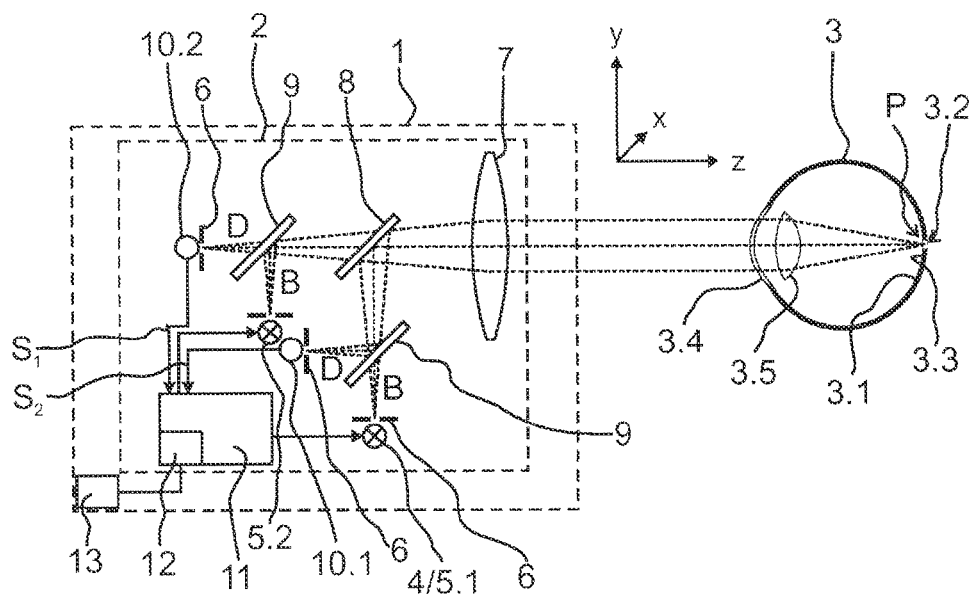
FIG. 1 shows an ophthalmological instrument having a fixation monitoring device.

FIG. 1 is a schematic diagram showing an ophthalmological instrument 1, for example, a refractive laser, having a fixation monitoring device 2 for monitoring the fixation of an eye 3. The fixation monitoring device 2 comprises, for example, an approximately point-shaped fixating light source 4 which simultaneously serves as a first measurement light source 5.1, a second measurement light source 5.2, pinholes 6 associated with the light sources 4 and 5, imaging optics 7, a dichroic color splitter 8, two color-neutral beamsplitters 9, two photodetectors 10.1 and 10.2, a pinhole 6 likewise being associated, respectively, therewith, and a controlling and evaluating unit 11 having an output interface 12. The output interface 12 is connected, for example, to a piezo buzzer as output unit 13. The fixating light source 4 emits, for example, exclusively visible light having a fixating wavelength $\lambda_F$ which is also used as first measurement wavelength $\lambda_1 : \lambda_F = \lambda_1 = 590$ nm. The second measurement light source 5.2 emits, for example, exclusively invisible infrared light having a second wavelength $\lambda_2 = 1050$ nm. The color splitter 8 is designed in such a way that it is penetrated by the first measurement wavelength $\lambda_1$ but reflects the second measurement wavelength $\lambda_2$. The two light sources 4/5.1 and 5.2 are adjusted, for example, electronically to a specified ratio of the light intensities of the two measurement wavelengths $\lambda_1, \lambda_2$. Alternatively, the relative intensity can be determined based on a reference measurement.

When the light sources 4 and 5 are switched on by the controlling and evaluating unit 11, the pinholes 6 and the optics 7 image the light sources 4, 5 in a point-shaped manner on a common point P on the fundus 3.1 via the beamsplitters 8 and 9 when the patient's eye 3 fixates the fixating light source 4. Depending upon the position of the eye 3, this point P can lie on the fovea 3.2 (particularly the foveola) or in the region of the rest of the retina 3.3. The pinholes 6 in front of the detectors 10 are arranged in a respective plane conjugate to the illuminated point P so that detection takes place confocally in the detectors 10 in this embodiment example. Because of the coupling of the illumination beam paths B and the detection beam paths D by means of the beamsplitters 8 and 9, all of the light sources 4, 5 appear to lie at the same location visually from the view point of the eye 3. In connection with the confocal detection, detectors 10 acquire exclusively light from the same point P in a corresponding manner and generate electric signals $S_1$, $S_2$ therefrom which separately represent the acquired light intensities of the two measurement wavelengths $\lambda_1, \lambda_2$.

The fixating and measurement wavelengths $\lambda_1$, $\lambda_2$ satisfy the condition of a reflection which differs in strength between the fovea 3.2 and the region of the rest of the retina 3.3 and in particular the condition respecting different ratios of their reflectance factors when reflected at the fovea 3.2 and retina 3.3, respectively. Accordingly, their relative spectral reflectivity differs with respect to the fovea 3.2 and retina 3.3:

$$R_{\lambda 1, Retina}/R_{\lambda 2, Retina} \neq R_{\lambda 1, Fove(ol)a}/R_{\lambda 2, Fove(ol)a}.$$

For fixation monitoring, the controlling and evaluating unit 11 switches on the light sources 4 and 5 permanently and evaluates the two electric signals $S_1$, $S_2$ by digitizing them and putting them in ratio to one another. In alternative embodiments (not shown), this can also be carried out in an analog-electrical manner. The controlling and evaluating unit 11 compares the resulting quantity $Q=S_1/S_2$, for example, with a predetermined threshold value above which a reflection at the fovea 3.2 or foveola (not shown) can be deduced based on the different reflectance factor. For example, the fovea 3.2 reflects the first measurement wavelength $\lambda$, significantly more strongly than measurement wavelength $\lambda_2$ because of its yellow pigmentation. As a result, the relative reflectance factor and, therefore, the measurable intensity of the first measurement wavelength $\lambda_1$ is greater when reflected at the fovea 3.2 than when reflected at the rest of the retina 3.3. Approximately the opposite reflection behavior applies to measurement wavelength $\lambda_2$.

Accordingly, it can be determined based on the ratio of measured light intensities of the two measurement wavelengths $\lambda_1$, $\lambda_2$ whether the measured reflection takes place at the fovea 3.2 or in the region of the rest of the retina 3.3. Insofar as the eye 3 fixates the fixating light source 4, the target P of the point-shaped imaging of the fixating light source 4 and, therefore, also the location of the reflection measured in detectors 10 lies on the fovea 3.2. By comparing with the threshold value, the controlling and evaluating unit 11 can determine whether or not a correct fixation existed at the time of measurement. Since the measurement and the comparison can be carried out with high accuracy (image processing is not necessary), the result signal can be outputted with a short response time. Of course, the quotient of the electric signals can be inverted depending on the wavelength that is used: $Q=S_2/S_1$. Depending on how the quotient is formed, the fixation can be identified based on whether the predetermined threshold is exceeded or not reached.

Insofar as the resulting quantity is less than the threshold, the controlling and evaluating unit 11 in the present embodiment example outputs a 1-level as digital electric result signal via interface 12. The output unit 13 then generates an audible alert so that the operator and the patient are alerted to the loss of fixation. If the resulting quantity is greater than or equal to the threshold value, a 0-level is generated as result signal. Accordingly, the audible alert is not emitted or is switched off if it was switched on previously.

In alternative embodiments (not shown) the result signal can be used alternatively or in addition to the described output unit 13 by a control unit (not shown) of the ophthalmological instrument 1 to interrupt an examination and/or a treatment as soon as the result signal indicates a loss of fixation. Additionally or alternatively, it is also possible to automatically trigger an examination and/or treatment when it is determined based on the result signal that the fixating light source 4 is correctly fixated by the eye 3.

In order to prevent a random eye movement being identified as fixation, an additional condition can be imposed whereby the identified fixation must exist for a minimum duration before a consequence is triggered. A minimum duration can be checked in the fixation monitoring device 2 itself or in a subordinated manner in the ophthalmological instrument 1. For example, the controlling and evaluating unit 11 can initialize a time monitoring counter when a comparison result indicating fixation is determined for the first time. A result signal indicating fixation is only generated when fixation has been maintained uninterruptedly for a minimum duration of one second, for example.

Instead of dichroic color splitters 8, neutral splitters can be combined with color splitters, gratings and/or prisms (not shown) to select the measurement wavelengths. In other embodiments (not shown), more than two measurement wavelengths can be used. In this case, three or more electric signals S are measured and, for example, put in a ratio by pairs. Then, in order to identify a correct fixation, for example, each of the quotients determined in this manner is compared separately with a respective threshold. A correct fixation is then indicated in the result signal only when each of the specified conditions (threshold is exceeded or is not reached) is met.

Pinholes 6 in front of the detectors 10 can be omitted (not shown) when the detectors 10 have a small aperture. The detectors 10 are then arranged in a confocal plane instead of pinholes 6. For example, an individual pixel of a confocally arranged spatially resolving sensor can be used without a pinhole 6 as confocal detector 10.

In other embodiment forms (not shown), the imaging optics 7 can be constructed in such a way by means of a motor control that they can be adjusted to different visual distances of the eye 3. To this end, the controlling and evaluating unit 11 is connected to the motor control in these kinds of embodiment forms for influencing the motor control.

Figure 2:
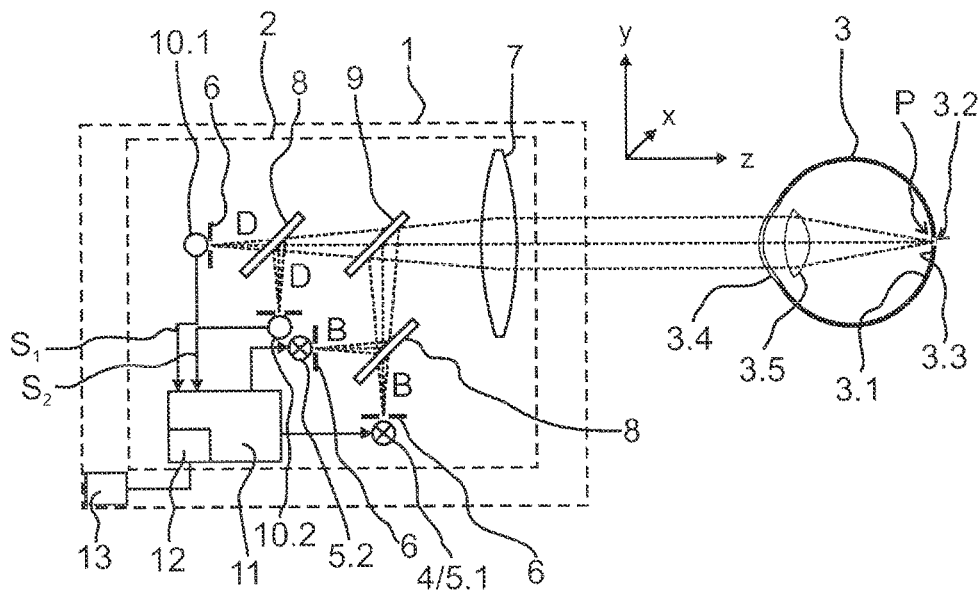
FIG. 2 shows another fixation monitoring device.

FIG. 2 shows an alternative embodiment form in which the detectors 10 are concentrated on a first color splitter 8 and the light sources 4, 5 are concentrated on a second color splitter 8. The illumination beam path B and the detection beam path D are coupled at a neutral splitter 9. For the rest, reference is had to the description referring to FIG. 1.

Figure 3:
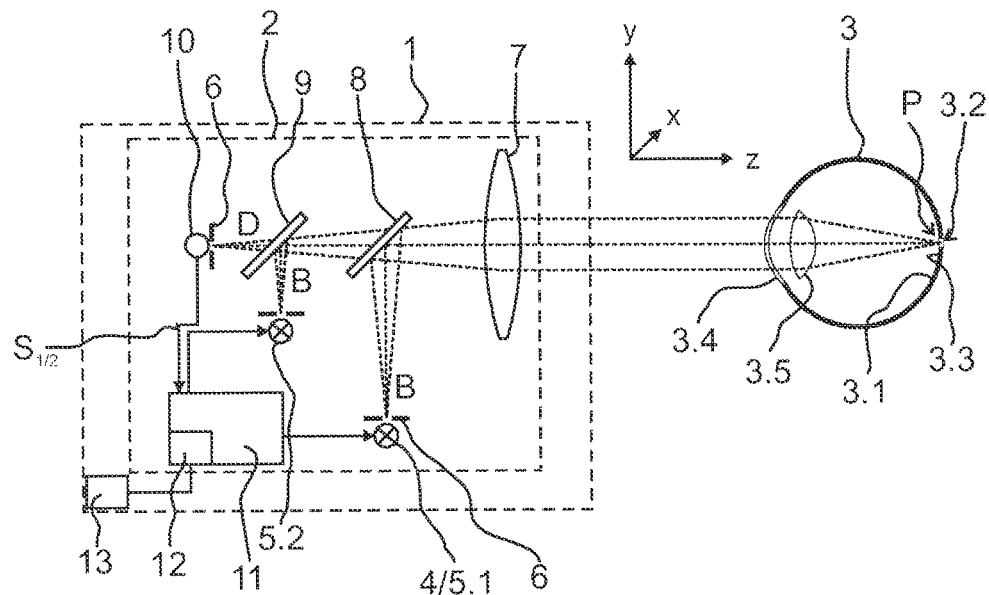
FIG. 3 shows a schematic diagram for the measurement light sources of this fixation monitoring device.
Figure 4:
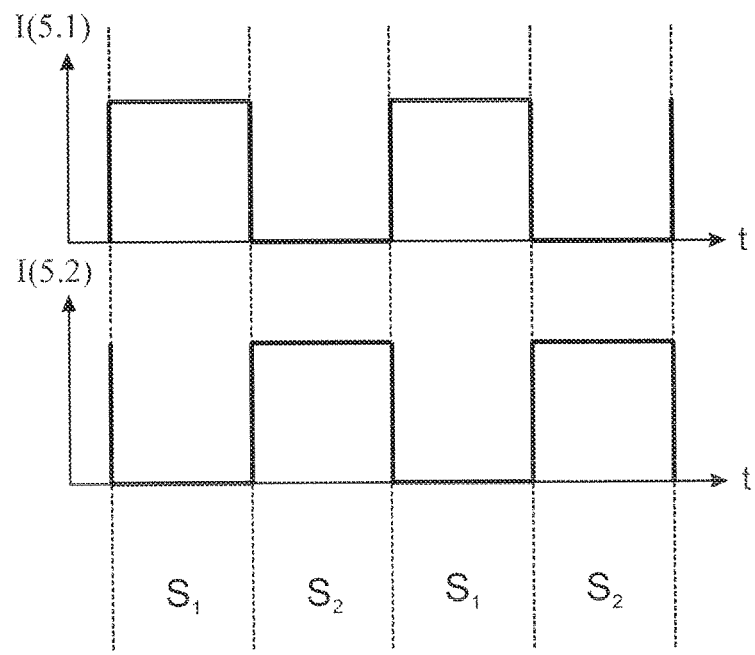
FIG. 4 shows a third fixation monitoring device.

FIG. 3 shows a fixation monitoring device 2 which substantially corresponds to the embodiment form according to FIG. 1. However, in contrast to the latter only one individual detector 10 is provided for acquiring the light of the two measurement wavelengths $\lambda_1$, $\lambda_2$. The detector 10 emits only one individual electric signal $S_{1/2}$. The two measurement light sources 5.1, 5.2 and therefore also the fixating light source 4 are intensity-modulated for purposes of separation. Subsequently, they blink at a high frequency. This can be carried out at the same frequency or at different frequencies for both measurement light sources 5.1 and 5.2. In the former case, the modulation takes place with offset phase, which is illustrated schematically in FIG. 4. In this case, the detector 10 acquires either one or the other measurement wavelength $\lambda_1$, $\lambda_2$ in a phase-sensitive manner so that the electric signal $S_{1/2}$ is interpreted by the controlling and evaluating unit 11 by blocks as first signal $S_1$ or as second signal $S_2$. In the second case mentioned above regarding modulation with different modulation frequencies, it is necessary to electronically separate the detected intensities of the two measurement wavelengths $\lambda_1$, $\lambda_2$, for example, by means of lock-in technique in which the modulation signal is used as reference. At lease the modulation frequency of the visible fixating light source 4 and first measurement light source 5.1 is advisably high enough in both types of modulation so that the eye 3 does not perceive any modulation (e.g., 50 Hz, 100 Hz, or 1 kHz). In particular, the modulation at different frequencies can be combined with a static color selection by means of beamsplitters and/or filters and/or gratings and/or prisms.

Figure 5:
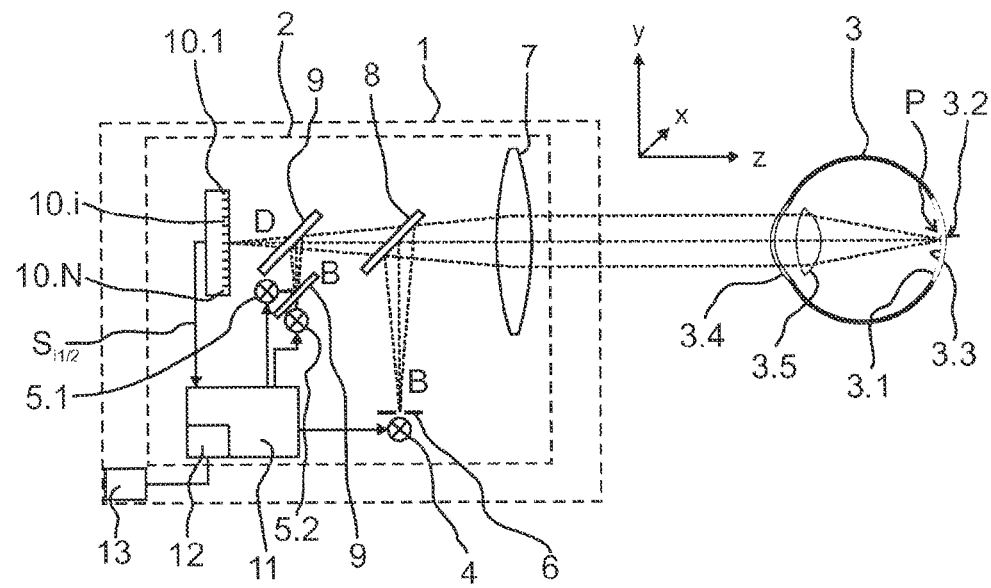
FIG. 5 shows a fourth fixation monitoring device.

FIG. 5 shows a fixation monitoring device 2 which substantially corresponds to the embodiment form according to FIG. 2. However, in contrast to the latter, a two-dimensional array of individual detectors 10.$i$ (i=1 ... N, e.g., N=256) and measurement light sources 5.1 and 5.2 which are imaged in a correspondingly two-dimensional manner in the fundus 3.1 are provided in addition to a separate fixating light source 4 which is imaged in a point-shaped manner in the fundus 3.1. The two light sources 5.1 and 5.2 are adjusted, e.g., electronically, to a predetermined ratio of the light intensities of the two measurement wavelengths $\lambda_1$, $\lambda_2$. Alternatively, the relative intensity can be determined based on a reference measurement. From the view point of the eye 3, the two-dimensional measurement light sources 5.1 and 5.2 (shown in white in the fundus 3.1) completely surround the point-shaped fixating light source 4. From the point of view of the fixation monitoring device 2, the individual detectors 10.$i$ look at different locations of the fundus 3.1 and accordingly allow the position of the fovea 3.2 (or particularly the foveola) to be determined based on the intensities of the differently reflected measurement wavelengths $\lambda_1$, $\lambda_2$. To this end, the measurement light sources 5.1 and 5.2 are operated with intensity modulation as was described above with reference to FIG. 3. The fixating light source 4 is permanently illuminated. By measuring separate electric signals $S_{i, 1/2}$ for each individual detector 10.$i$ and taking their ratio detector by detector, it can be ascertained for each individual detector 10.$i$ whether or not the fovea 3.2 was imaged thereon. The instantaneous gaze direction of the eye 3 can be determined from the relative position of the image of the fovea 3.2 in the detector array and can be outputted via the output interface 12. In a case such as this, evaluating units (not shown) of the ophthalmological instrument 1 are advisably connected to the interface 12 for purposes of further processing. When the eye 3 fixates the fixating light source 4 only in an out-of-focus manner, the fovea 3.2 is imaged on the relevant detector 10.$i$, for example, as a blurred spot. A center of the spot is then determined as location of the image of the fovea 3.2, for example.

Figure 6:
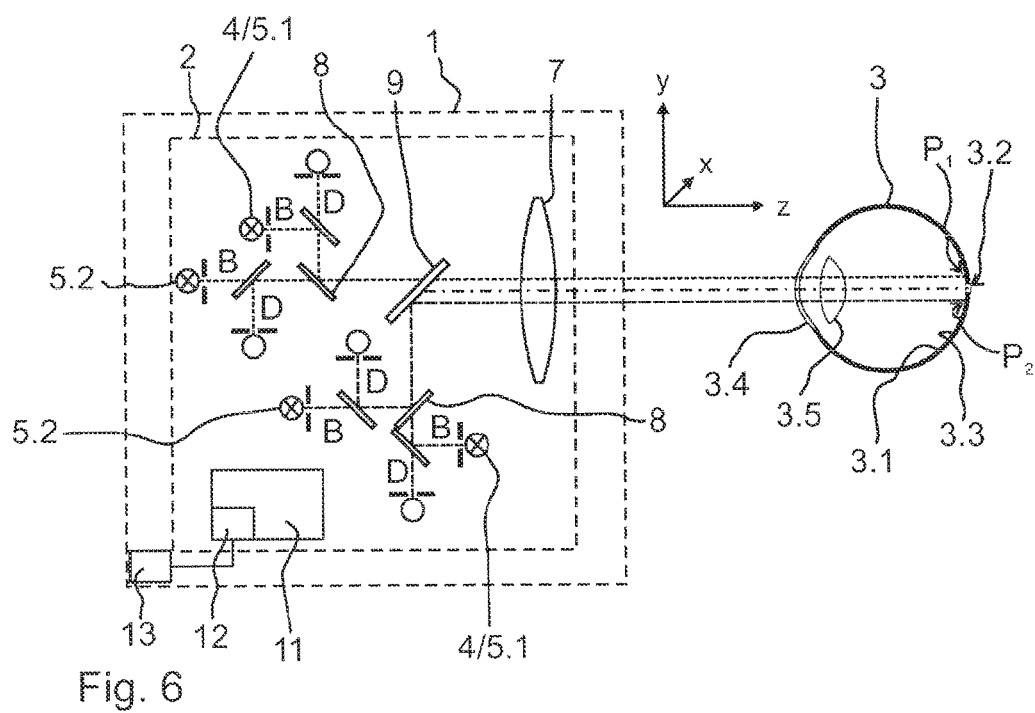
FIG. 6 shows a fifth fixation monitoring device.

FIG. 6 also shows a fixation monitoring device 2 which substantially corresponds to the embodiment form according to FIG. 1, and reference is had to the description thereof. In contrast to the latter, however, a plurality of independent illumination and detection beam paths B, D are provided each with its own fixating light source 4. For the sake of clarity, only two illumination and detection beam paths B, D are shown. The same pair (triplet, quadruplet, etc. in case of more than two wavelengths) of measurement wavelengths $\lambda_1$, $\lambda_2$ can be used in all of the beam paths B, D. This arrangement likewise allows spatially resolved fixation detection because the fixating light sources 4 fixated by the eye 3 can be identified insofar as there is any fixation.

Figure 7:
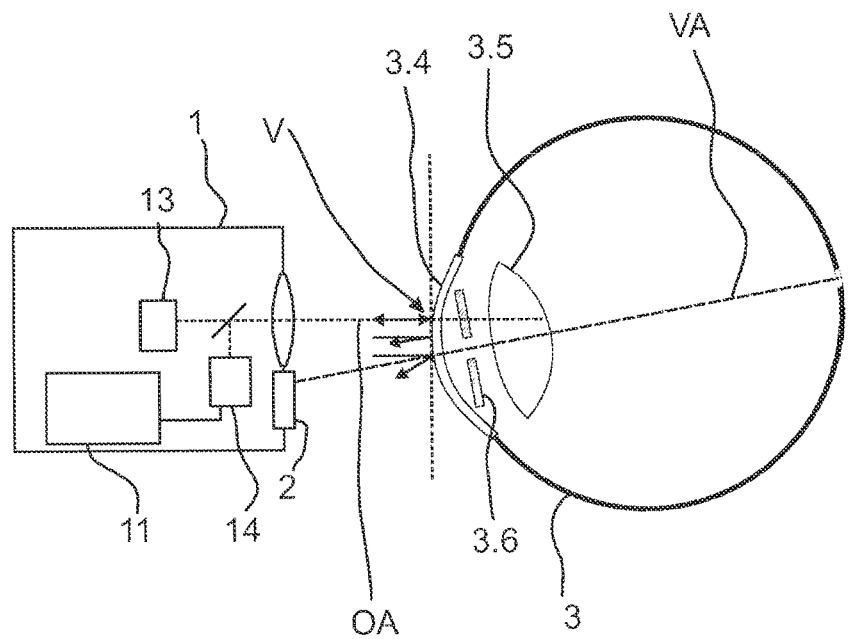
FIG. 7 shows another ophthalmological instrument.

Finally, FIG. 7 shows a schematic diagram of an ophthalmological instrument 1, for example, a femtosecond laser for surgical treatment, which is outfitted, apart from a fixation monitoring device 2, with a light source 13 for collimated illumination of the cornea 3.4 and with a camera 14 for acquiring an image particularly of the pupil 3.6. The controlling and evaluating unit 11 can measure a position of the vertex V of the cornea 3.4 with reference to the optical axis OA of the camera 14 (identical to the optical axis of the laser, not shown) in the coordinate system of the laser (typically Cartesian coordinates x/y/z, with z in direction of the optical axis of the laser) by generating a Purkinje reflex in a known manner by means of the light source 13 and camera 14 and localizing the instantaneous vertex on this basis. The fixating point for the patient (in this case, fixating light source (not shown) of the fixation monitoring device 2) lies off the optical axis OA. The collimated light striking the cornea 3.4 parallel to this axis is reflected to the camera 14 only from the highest point on the cornea 3.4 (i.e., the vertex V). Reflections from other locations do not reach the camera 14 (indicated by arrows). When the controlling and evaluating unit ascertains by means of the fixation monitoring device 2 that the eye 3 fixates the fixating light source (not shown here) of the fixation monitoring device 2, an image of the pupil 3.6, for example, is acquired in addition. The relative position of the instantaneous vertex V (fixation vertex) relative to a reference point which is stationary with respect to the eye, for example, relative to the centroid or center of the pupil 3.6 or the limbus, is then determined in the form of a two-dimensional vector based on the recorded image and is stored and/or outputted, or is stored and/or outputted in the form of the entire recorded image as reference for the fixated state.

In all of the embodiment forms, constructions which unambiguously define a point to be sighted, for example, cruciform fixating light sources, can be used instead of point-shaped fixating light sources.

Figure 8:
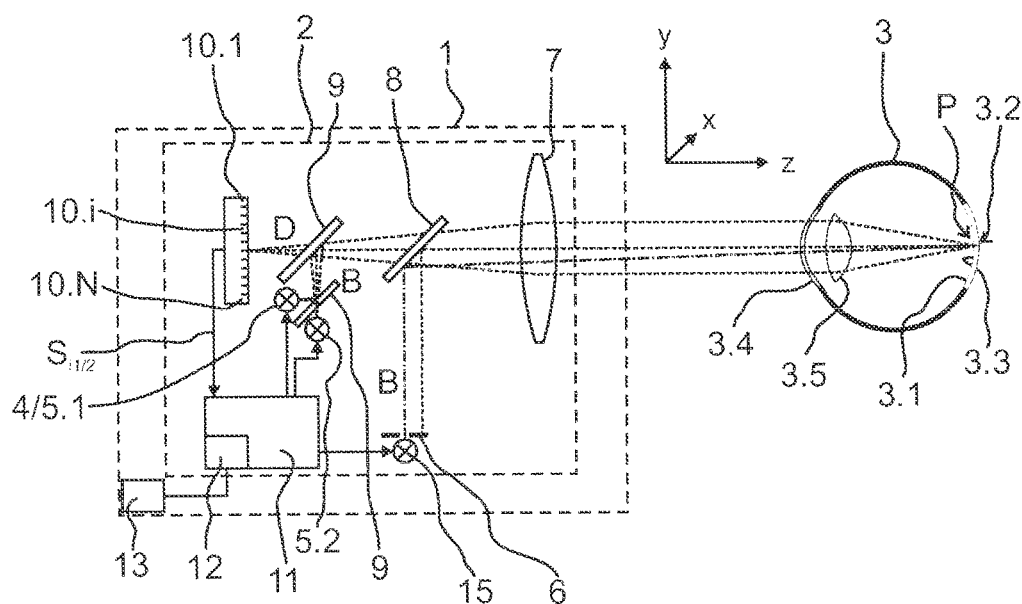
FIG. 8 shows a sixth fixation monitoring device.

FIG. 8 shows an embodiment form of a fixation monitoring device 2 having an additional fixating light source 15 which is arranged off the optical axis of the detector 10. This embodiment form allows individual norming on the eye 3. When the gaze VA of the eye 3 is directed to the first fixating light source 4, first reference signals can be determined by means of the detector 10 for the fixated state of the eye 3 because the measurement wavelengths are reflected at the fovea 3.2. When the gaze VA of the eye 3 is directed to the additional fixating light source 15, second reference signals can be determined by means of the detector 10 for the non-fixated state of the eye 3 because the measurement wavelengths are reflected offside of the fovea 3.2. A first reference value can be determined from the first reference signals and a second reference value can be determined from the second reference signals. The arithmetical mean of the two reference signals can be specified, for example, as a threshold for identifying fixation.

Figure 9:
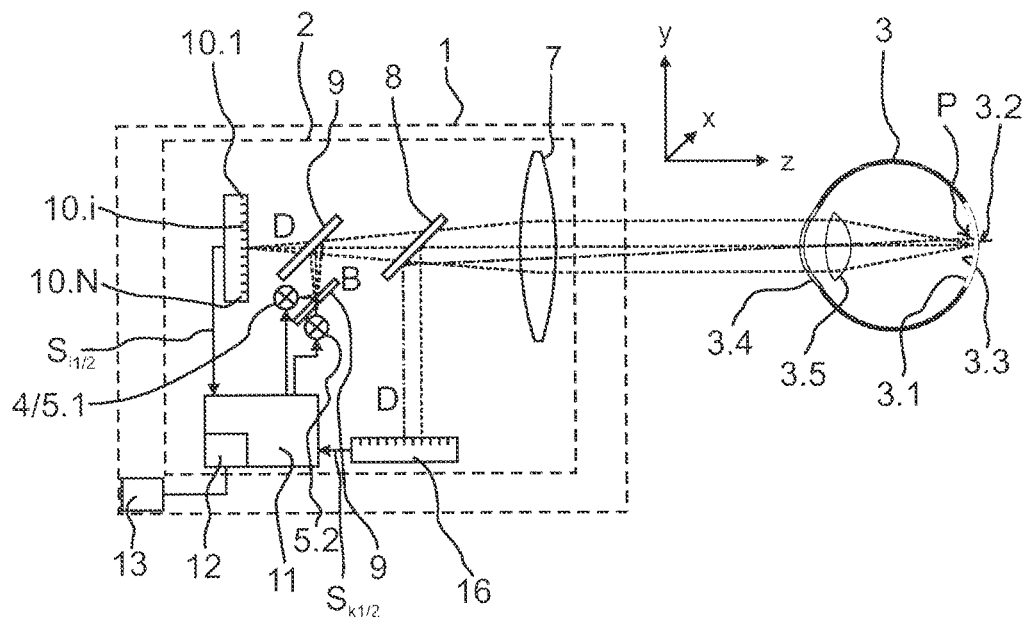
FIG. 9 shows a seventh fixation monitoring device.

A modified embodiment form offering the possibility of norming is shown in FIG. 9. In this case, light that was reflected at a different location than the light received by the first detector 10 is received by a second detector 16 at the same time as the first detector 10. When the gaze VA of the eye 3 is directed to the fixating light source 4, first reference signals can be determined by means of the first detector 10 for the fixated state of the eye 3 because the received measurement wavelengths were reflected at the fovea 3.2, and second reference signals can be determined by means of the second detector 16 for the non-fixated state of the eye 3 because the received measurement wavelengths were reflected offside of the fovea 3.2.

Figure 10:
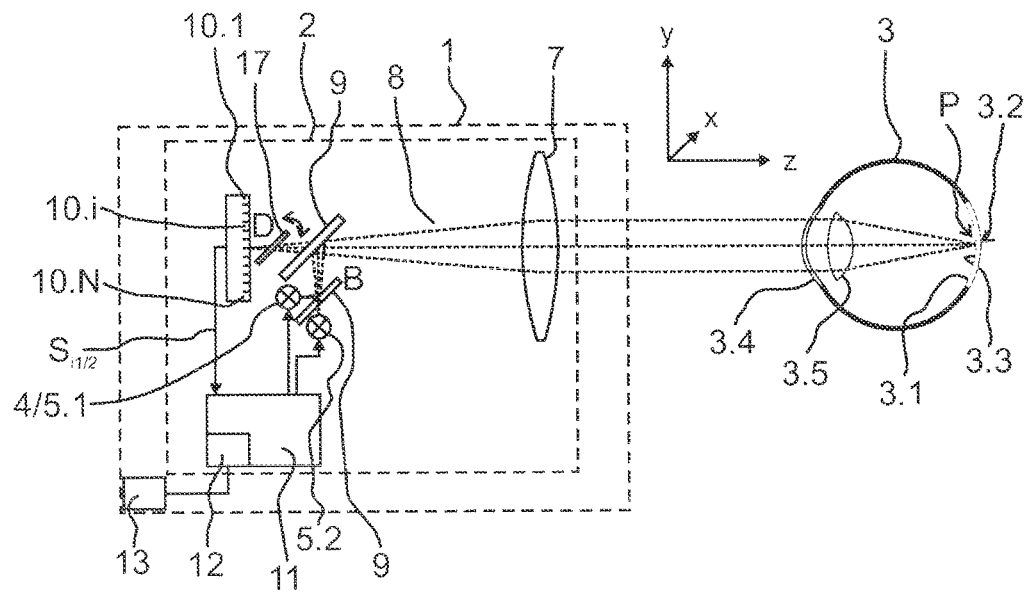
FIG. 10 shows an eighth fixation monitoring device.

FIG. 10 shows another embodiment form affording the possibility of forming in which an adjustable beam deflecting device 17 is arranged in the detection beam path. By adjusting the beam deflecting device 17, the detection beam path D can be deflected so that detector signals can be received from different locations on the fundus. When the detection beam path D is directed to the fovea 3.2, first reference signals for the fixated state of the eye 3 can be determined by means of detector 10 because the received measurement wavelengths were reflected at the fovea 3.2. When the detection beam path D is directed to a location on the rest of the retina 3.3, second reference signals can be determined by means of the first detector 10 for the non-fixated state of the eye 3 because the received measurement wavelengths were reflected at the retina 3.3.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

REFERENCE NUMBERS 1 ophthalmological instrument
2 fixation monitoring device
3 eye
3.1 fundus
3.2 fovea
3.3 retina
3.4 cornea
3.5 eye lens
3.6 pupil
4 fixating light source
5 measurement light sources
5.1 first measurement light source
5.2 second measurement light source
6 pinhole
7 optics
8 color splitter
9 neutral splitter
10 detector
10.1 first detector
10.2 second detector
11 controlling and evaluating unit
12 output interface
13 light source
14 camera
15 additional fixating light source off the optical axis
16 second detector
17 adjustable beam deflecting device
P point on the fundus
B illumination beam path
D detection beam path
OA optical axis of camera and laser
VA visual axis

The invention claimed is:

1. A fixation monitoring device for an ophthalmological instrument, comprising:
   a fixation light source configured to emit visible light;
   optics configured to image the fixating light source on a fundus; and
   a detector unit configured to implement spectroscopic detection of a fixation of an eye, the spectroscopic detection being based on difference in spectral reflectivity between a fovea of the eye and a surrounding retina of the eye.

2. The fixation monitoring device according to claim 1; wherein the detector unit includes:
   at least one measurement light source for emitting light of at least two wavelengths which have a different ratio of reflectance factors when reflected at a fovea than when reflected at the rest of a retina;
   optics for imaging the measurement light source on at least a portion of the fundus; and
   at least one detector for separately acquiring the intensities of the two wavelengths as respective detector signals after a reflection at the fundus.

3. The fixation monitoring device according to claim 2, further comprising:
   an evaluating unit configured to:
      determine a ratio of the two detector signals;
      compare the ratio with a specified value or a specified value range; and
      output a result signal depending on the results of the comparison.

4. The fixation monitoring device according to claim 2; wherein a beam path to the at least one detector and a beam path to the at least one measurement light source are partially identical.

5. The fixation monitoring device according to claim 2, further comprising:
   a two-dimensional array of detectors having respective detector signals; and
   a correspondingly two-dimensional construction of the measurement light source for emitting exclusively invisible measurement wavelengths;
   wherein the measurement light source at least partially surrounds the fixating light source from a view point of a patient.

6. The fixation monitoring device according to claim 1, further comprising a plurality of measurement light sources which are configured to be imaged in the fundus in a point-shaped manner;
   wherein each measurement light source has two wavelengths having a different ratio of reflectance factors when reflected at a fovea than when reflected at the rest of a retina.

7. The fixation monitoring device according to claim 1, wherein the optics is configured to implement adjustable projection of the fixation light source at different visual distances.

8. The fixation monitoring device according to claim 1; wherein the fixating light source is located on the optical axis of the spectroscopic detection arrangement; and
   wherein another fixating light source is located off the optical axis of the spectroscopic detection arrangement.

9. The fixation monitoring device according to claim 1, further comprising:
   an evaluating unit which identifies a state of fixation of a fixating target by an eye, and subsequently:
      triggers an image recording of the eye or a treatment of the eye; and/or
      engages eye movement tracking.

10. An ophthalmological instrument having a fixation monitoring device according to claim 1.

11. A method for monitoring a fixation of an eye comprising:
   a step of implementing spectroscopic detection of a fixation of an eye, the spectroscopic detection being based on difference in spectral reflectivity between a fovea of the eye and a surrounding retina of the eye.

12. A method for monitoring a fixation of an eye, comprising:
   illuminating at least a portion of the fundus by a measurement light source by light of two wavelengths which have a different ratio of reflectance factors when reflected at a fovea than when reflected at a retina;
   acquiring intensities of the two wavelengths separately by at least one detector as respective detector signal after reflection at a fundus;
   determining a ratio of the two detector signals;
   comparing the ratio with a specified value or a specified value range; and
   outputting a result signal depending on the results of the comparison.

13. The method according to claim 12, further comprising:
ascertaining that an eye fixates a fixating target, whereupon:
an image recording of the eye or a treatment of the eye is triggered; and/or
eye movement tracking is engaged.

14. The method according to claim 12, further comprising:
acquiring another measurement value and/or an image during the detection of the intensities of the measurement wavelengths, and
valuating and/or weighting the another measurement value and/or an image based on the ratio of the detector signals.

15. The method according to claim 12;
wherein the value or value range used in the comparison corresponds to a reflection of the two wavelengths at the fovea.

16. The method according to claim 12, further comprising modulating the fixating light source depending on the result signal.

17. The method according to claim 12, further comprising:
a step comprising:
modulating an intensity the at least one measurement light source with different frequencies for the two wavelengths; and
detecting the reflected wavelengths in a common detector;
wherein an electronic separation into the detector signals is carried out subsequently; or
a step comprising:
modulating an intensity the at least one measurement light source with an identical frequency for the two wavelengths with offset phases; and
phase-sensitive detection of the two wavelengths in a common detector.

18. The method according to claim 12, further comprising:
implementing confocal detection in the at least one detector.

19. The method according to claim 12, further comprising:
recording an image of an iris by a camera for determining a relative position of a pupil relation to a vertex of a cornea.

20. The method according to claim 12, further comprising:
implementing pulsed operation of the at least one measurement light source.

21. The method according to claim 12, further comprising:
determining a first reference value for the ratio of the detector signals in case of reflection at the fovea; and
determining a second reference value for the ratio of the detector signals in case of reflection at the retina.

22. A non-transitory storage medium storing a computer program, when executed, causing a fixation monitoring device to implement a fixation monitoring method, the fixation monitoring method comprising:
instructions which, when carried out by the fixation monitoring device, implement the method according to claim 12.

23. An evaluating unit configured to implement the method to claim 12.

24. The fixation monitoring device according to claim 3;
wherein the value or value range used in the comparison corresponds to a reflection of the two wavelengths at the fovea.

25. The fixation monitoring device according to claim 3;
wherein the fixating light source is modulated depending on the result signal.

26. The fixation monitoring device according to claim 2;
wherein:
an intensity of the at least one measurement light source is modulated with different frequencies for the two wavelengths;
the reflected wavelengths are detected in a common detector; and
an electronic separation into the detector signals is carried out subsequently; or
wherein:
an intensity of the at least one measurement light source is modulated with an identical frequency for the two wavelengths with offset phases; and
phase-sensitive detection of the two wavelengths in a common detector is performed.

27. The fixation monitoring device according to claim 2;
wherein the at least one detector is configured for confocal detection.

28. The fixation monitoring device according to claim 2, further comprising:
a camera which is configured to record an image of an iris for determining a relative position of a pupil relation to a vertex of a cornea.

29. The fixation monitoring device according to claim 2;
wherein the at least one measurement light source is configured for pulsed operation.

30. The fixation monitoring device according to claim 3;
wherein a first reference value for the ratio of the detector signals is determined in case of reflection at the fovea; and
wherein a second reference value for the ratio of the detector signals is determined in case of reflection at the retina.

* * * * *